(12) United States Patent
Kreindel et al.

(10) Patent No.: US 8,135,475 B2
(45) Date of Patent: Mar. 13, 2012

(54) METHOD AND DEVICE FOR COLLAGEN GROWTH STIMULATION

(75) Inventors: Michael Kreindel, Yokneam Illit (IL); Lion Flyash, Nazareth-illit (IL)

(73) Assignee: Syneron Medical Ltd., Yokneam Illit (IL)

( * ) Notice: Subject to any disclaimer, the term of this patent is extended or adjusted under 35 U.S.C. 154(b) by 841 days.

(21) Appl. No.: 12/222,063

(22) Filed: Jul. 31, 2008

(65) Prior Publication Data
US 2009/0043247 A1 Feb. 12, 2009

Related U.S. Application Data

(60) Provisional application No. 60/935,224, filed on Aug. 1, 2007.

(51) Int. Cl.
*A61F 7/00* (2006.01)
(52) U.S. Cl. ............ 607/99; 607/101; 607/98; 607/150; 607/147; 604/13; 604/20; 604/21; 604/22
(58) Field of Classification Search .............. 607/98–99, 607/101, 150, 147; 604/13, 20–22
See application file for complete search history.

(56) References Cited

U.S. PATENT DOCUMENTS

| | | | |
|---|---|---|---|
| 5,755,753 | A | 5/1998 | Knowlton |
| 5,810,801 | A | 9/1998 | Anderson et al. |
| 5,860,951 | A * | 1/1999 | Eggers et al. .................. 604/510 |
| 6,224,592 | B1 * | 5/2001 | Eggers et al. .................. 606/32 |
| 6,309,387 | B1 | 10/2001 | Eggers et al. |
| 6,546,934 | B1 | 4/2003 | Ingle et al. |
| 2002/0077626 | A1 * | 6/2002 | Ellman et al. .................. 606/41 |
| 2003/0216719 | A1 | 11/2003 | Debenedictis et al. |
| 2005/0043726 | A1 | 2/2005 | McHale et al. |
| 2006/0036300 | A1 | 2/2006 | Kreindel |
| 2006/0259102 | A1 | 11/2006 | Slatkine |
| 2007/0288078 | A1 * | 12/2007 | Livneh ......................... 607/147 |

FOREIGN PATENT DOCUMENTS

| | | |
|---|---|---|
| DE | 199 29 713 A1 | 1/2001 |
| WO | 2005/094682 A1 | 10/2005 |

OTHER PUBLICATIONS

Liebl, H., "Stimulation of Cell Growth (Collagen-Induction-Therapy", Internet Article, [Online] May 23, 2007, XP002508164; Retrieved from the Internet: URL:http://web.archive.org/web/20071018115023/ dermaroller.de/CIT-findings.htm> [retrieved on Dec. 15, 2008].
The International Search Report for corresponding PCT International Application No. PCT/IL2008/001055; completed on Dec. 15, 2008, mailed on Jan. 29, 2009; three (3) pages.

* cited by examiner

*Primary Examiner* — Bhism Mehta
*Assistant Examiner* — Edelmira Bosques
(74) *Attorney, Agent, or Firm* — The Nath Law Group; Susanne M. Hopkins; William L. Klima

(57) ABSTRACT

The invention provides an applicator for skin treatment having one or more RF electrodes. An article is located between the electrodes, such as a roller or flexible belt containing one or more protruding pins electrically isolated from the RF electrodes. The invention also provides a system for skin treatment comprising the applicator of the invention and a control unit. The invention further provides a method of treating skin disorders in which a section of the skin is heated while, essentially simultaneously, piercing one or more holes in the heated section of the skin. The method of the invention may be used, for example, in collagen remodeling.

12 Claims, 4 Drawing Sheets

METHOD AND DEVICE FOR COLLAGEN GROWTH STIMULATION

CROSS-REFERENCE:

This is an application claiming the benefit under 35 USC 119(e) of U.S. Provisional Patent Application No. 60/935,224, filed on Aug. 1, 2007, the entire content of which is hereby incorporated by reference in its entirety.

FIELD OF THE INVENTION

This invention relates to electromagnetic energy skin treatment and, in particular, skin treatment for dermatological and cosmetic purposes.

BACKGROUND OF THE INVENTION

It is known that skin damage can stimulate the growth of new collagen. Uncontrolled skin damage may cause scarring, which is excessive collagen growth. However, controlled damage of the skin which is intentionally introduced can stimulate controlled re-growth of collagen in such a way as to improve the appearance of the skin. A well known method of controlled skin damage is ablating the epidermis using laser radiation with wavelengths having strong water absorption. Typical lasers used for epidermal ablation are $CO_2$ and Er:YAG lasers. U.S. Pat. No. 6,309,387 to Eggers et al. discloses ablation of the epidermis using RF current. This treatment significantly reduces wrinkles and improves skin appearance. The main disadvantages of skin resurfacing are the long healing period that can last for more than a month, and a high risk of dischromia. These disadvantages have reduced the popularity of ablative skin resurfacing.

Non-ablative skin resurfacing is based on heating the dermis up to a sub-necrotic temperature with simultaneous cooling of the skin surface. U.S. Pat. No. 5,810,801 to Anderson et al. describes the use of infrared laser radiation penetrating into the skin dermis with dynamic cooling of the skin surface using a cryogen spray. U.S. Pat. No. 5,755,753 to Knowlton describes a method of skin tightening using uni-polar or bi-polar RF electrodes to create skin heating in combination with cooling to generate a negative skin temperature gradient in which the dermis is hotter than the epidermis. The main barrier for introducing RF current is the stratum cornea, which should be hydrated by an electrolytic type of liquid prior the treatment. Non-ablative treatment is much safer and has no down time but the results of the treatment are less satisfactory.

A method described in US patent publication 20030216719 tries to retain the efficiency of ablative treatment coupled with a shorter healing time and with a lower risk of adverse effects. The device described in this patent publication coagulates fragments of the skin having a size in the range of tens of microns while keeping the distance between the fragments larger than the damaged zone. This treatment provides skin healing within a few days, but the results are very superficial and less satisfactory than with a $CO_2$ laser, even after multiple sessions.

SUMMARY OF THE INVENTION

Disclosed is a system and method for collagen growth stimulation. The method and the system use a combination of two different methods of stimulating collagen growth to provide a collagen remodeling process that is controlled and effective.

This method can be applied to a plurality of clinical treatments including different skin disorders, such as wrinkle treatment, skin tightening, skin rejuvenation, skin dischromia treatment, and others.

The system comprises a mechanical part creating spaced apart blind micro-holes in the skin with controlled size and surface density and one or more sources of energy providing skin heating.

Thus, in one of its aspects, the invention provides an applicator for skin treatment, said applicator comprising:
  (a) one or more RF electrodes adapted to be applied to skin surface; and
  (b) an article located between the electrodes, said article containing one or more protruding pins electrically isolated from the RF electrodes.

In another of its aspects, the invention provides a system for skin treatment, said system comprising:
  (a) an applicator for skin treatment, said applicator including:
    i) one or more RF electrodes adapted to be applied to skin surface; and
    ii) an article located between the electrodes said article containing one or more protruding pins electrically isolated from the RF electrodes; and
  (b) a control unit.

The invention also provides a method of treating skin disorders, said method comprising heating a section of the skin while, essentially simultaneously, piercing one or more holes in the heated section of the skin.

The invention still further provides a method of collagen remodeling, said method comprising:
  (a) puncturing a section of skin by one or more invasive pins, and introducing fragmental holes into the skin; and
  (b) stimulating collagen growth in the skin using an RF electrode and heating the skin.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
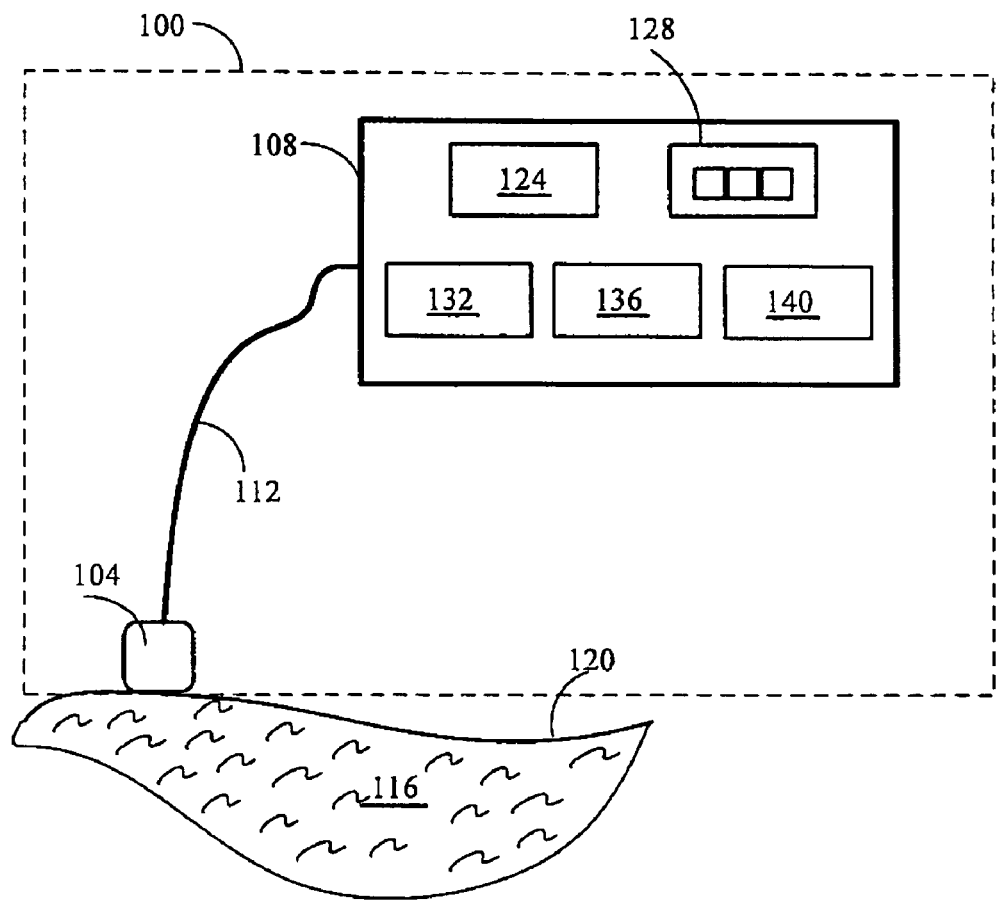
FIG. 1 is a schematic illustration of an exemplary embodiment of a system for skin treatment in accordance with the present method.

Reference is made to FIG. 1, which is a schematic illustration of an exemplary embodiment of a system for skin treatment in accordance with the present method. The system 100 includes an applicator 104 and a control unit 108 both of which will be described in detail below. A cable 112 connects the applicator 104 to the control unit 108. Applicator 104 is adapted to be applied to the skin 116 of an individual and moved over the skin 116 surface 120.

Control unit 108 includes an RF energy generator 124 that is connected to RF electrodes 204 (FIG. 2) in the applicator 104 via wires in cable 112. Control unit 108 has an input device such as a keypad 128 that allows an operator to input selected values of parameters of the treatment, such as the frequency, pulse duration and intensity of the RF energy. Control unit 108 optionally contains a processor 132 for monitoring and controlling various functions of the system. For example, processor 132 may monitor the electrical impedance between the electrodes 204 in the applicator 104, and determine the temperature distribution close to and at the target skin section. Processor 132 may also determine the parameters of the treatment based upon the impedance between electrodes 204 measurements.

Control unit 108 may include a source of power supply 136 that provides power to an optional light source located in applicator 104. In the course of operation, when RF is supplied to electrodes 204, the temperature of the electrodes may increase. Electrodes 204 can be cooled using thermoelectric coolers (not shown) or a cold fluid that has a temperature less than that of the skin surface. Control unit 108 may include a source 140 of such a fluid, and pump the fluid to the electrodes when needed.

Figure 2:
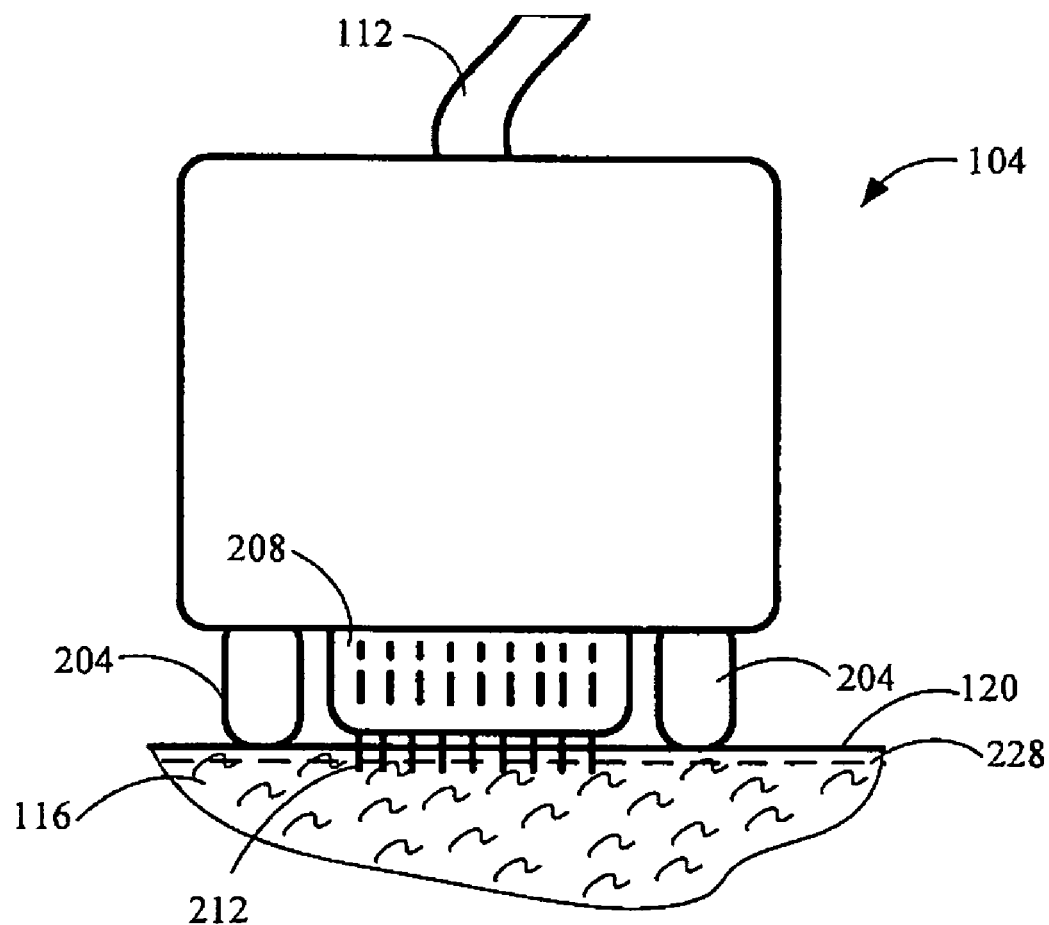
FIG. 2 is a schematic illustration of an exemplary embodiment of the applicator for use in the system of FIG. 1.

FIG. 2 is a schematic illustration of an exemplary embodiment of the applicator for use in the system of FIG. 1. Applicator 104 is shown applied to a skin surface 120. Applicator 104 contains one or more RF electrodes 204, but typically would have a pair of RF electrodes 204, and an article having a form of a roller 208 with pins 212 protruding and extending outwardly in radial direction, electrically isolated from RF electrodes. Article 208 is located between electrodes 204 and is made from an electrically insulating or dielectric material. The diameters of pins 212 are less than 0.5 mm and their length is not more than 3 mm. The typical length of the pins is 0.7 mm and the typical diameter is 0.1 mm. Any biocompatible material, for example, stainless steel, plastic material, and composite materials could be used for making the pins. The density of the pins should be high enough to provide uniform treatment of the treated skin surface. Typically, a pin density of 10-20 per square centimeter is sufficient for successful treatment results. Pins 212 made of metal may be inserted into the roller 208 insulating material. Alternatively, pins 212 may be formed from the same insulating material being an integral part of roller 208.

Figure 3:
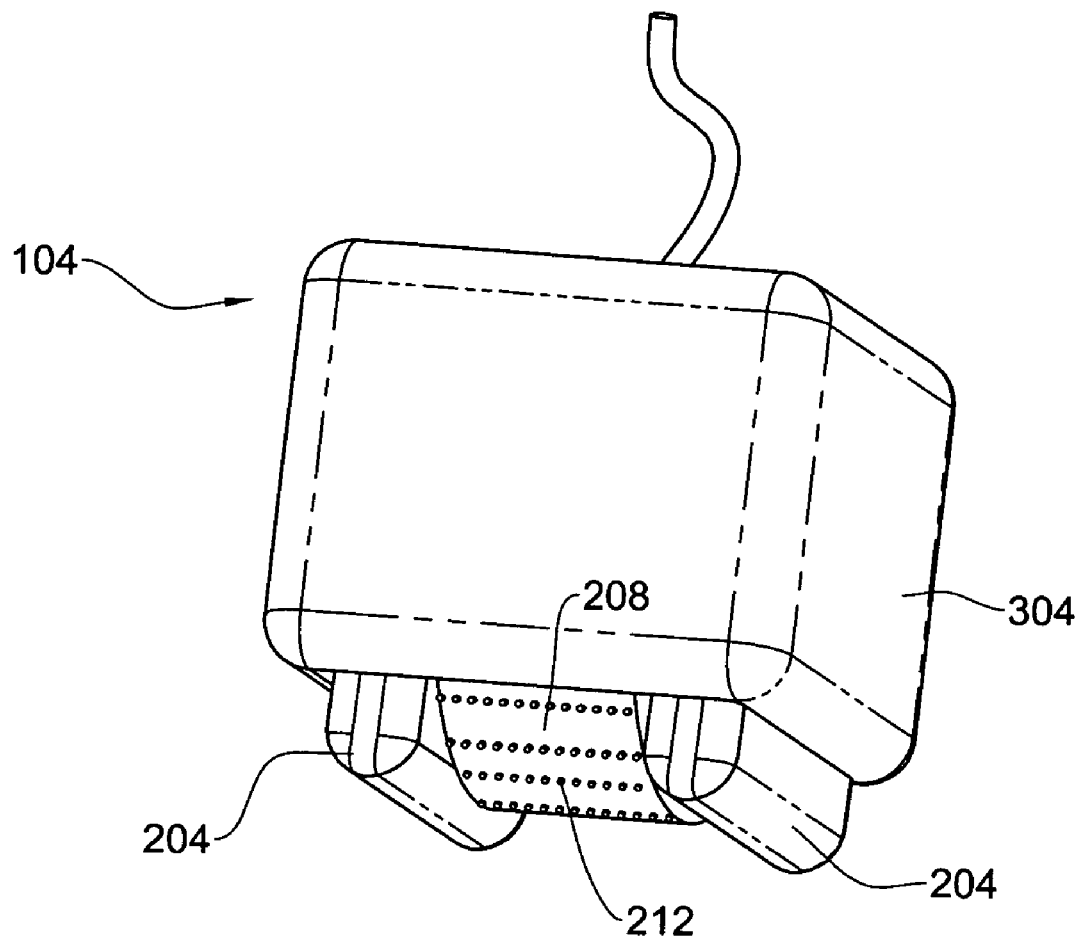
FIG. 3 is a schematic illustration of a perspective view of the applicator of FIG. 2.

FIG. 3 is a schematic illustration of a perspective view of the applicator of FIG. 2. FIG. 2 is a schematic illustration of an exemplary embodiment of the applicator for use in the system of FIG. 1. Applicator 104 has a body 304, which is convenient to hold and serves as a frame that contains a pair of RF electrodes 204, and article 208 having a form of a roller with protruding pins 212 electrically isolated from RF electrodes.

Figure 4:
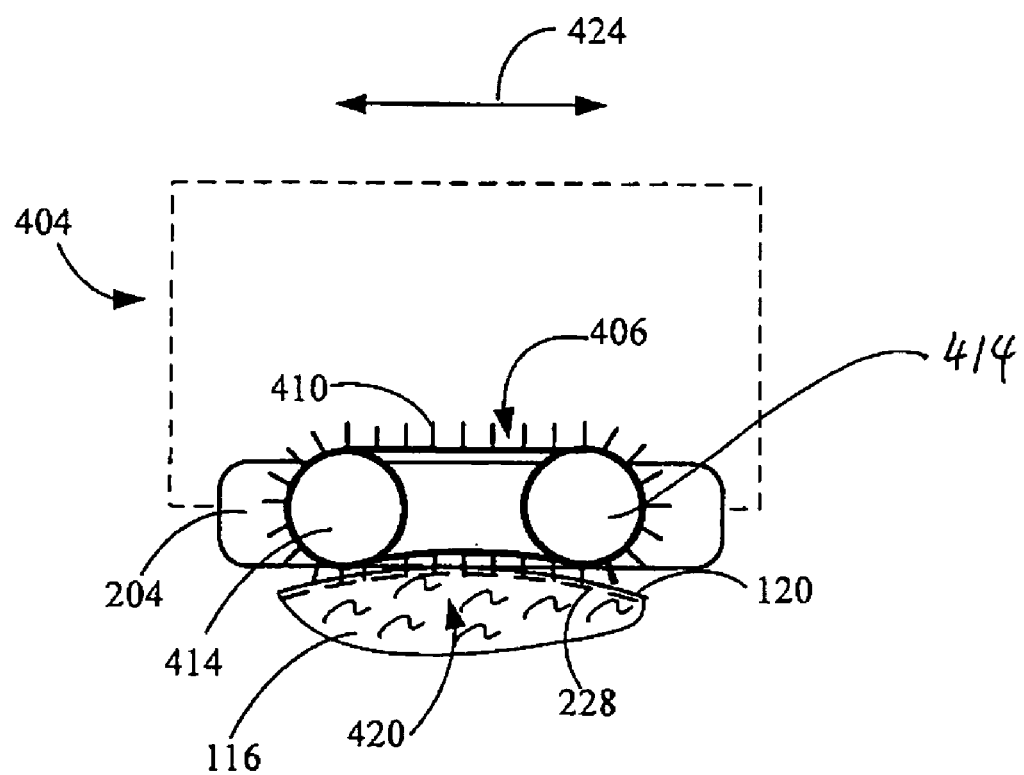
FIG. 4 is a schematic illustration of another exemplary embodiment of the applicator for skin treatment in accordance with the present method.

In an alternative embodiment shown in FIG. 4, the article has the form of an endless flexible belt 406 with pins 410 similar to pins 212 protruding from the belt. Belt 406 may be tensioned between two rollers 414 and, if necessary, conform to a treated section of skin 116. The distance between the rollers may be longer or shorter than the length of electrodes 204.

In use, applicator 104 or 404 is applied to skin such that RF electrodes 204 contact the skin 116 surface 120. Following this, applicator 104 is moved over skin 116, maintaining contact with skin surface 120. As applicator 104 is moved over the skin surface 120, article 208 (roller 208) or belt 406 rolls over the skin surface 120. Pins 212 or 410 puncture the skin and create blind holes in it, penetrating into the skin to reach a collagen layer 228 located at a depth of over 70 microns below the skin surface. Simultaneously RF energy is supplied to electrodes 204 and an RF current is made to flow between the electrodes 204 through collagen layer 228 of the skin. RF electrodes 204 deliver an RF current to the skin section with holes created in it by pins 212 or 410 and provide heating of the collagen structure 228. The RF power applied should be sufficient to heat a treated skin section by at least 5 (five) degrees C. The optimal skin heating is 10-20 degrees C. over the normal skin temperature. The RF power is preferably in the range of 10-500 W, more preferably 20-100 W. The RF current frequency is in the range of 0.2-100 MHZ, with a typical operating range of 1-10 MHz. Control unit 108 regulates and switches ON or OFF supply of RF power to electrodes 204 by monitoring the impedance between electrodes 204.

Pins 212 or 410 made of an isolating or dielectric material have a resistance higher than that of the skin and the damaged section of the skin around the pin/s. The lower conductivity of the plastic or dielectric in the interior of blind holes causes the current density to be maximal around the circumference of the holes. Holes produced by pins 212 or 410 are spaced apart from each other and there is no contact between them. The holes damage a small fragment of the skin 116. The high density of RF current around the punctured holes heats the fraction of the skin around each hole more strongly and further stimulates collagen growth.

As noted above, electrodes 204 may be shorter or longer than the punctured skin section. FIG. 4 illustrates electrodes 204 that are longer than the punctured skin section 420 typically located between rollers 414. Applicator 404 continues its movement to the next skin section to be treated. For example, in one of the directions indicated by arrow 424, leaving the blind holes created by pins 410 filled with air. The lower conductivity of the air in the interior of blind holes causes the current density to be maximal around the circumference of the holes. The high density of RF current around the punctured holes heats more strongly the fraction of the skin around each hole, and longer electrodes extend the treatment time, further stimulating collagen growth.

The treated skin surface 120 is affected by rolling the article over the skin. Pins of the article penetrate skin 116 and should be sterilized before each treatment. In order to avoid this and simplify the treatment process, both roller 208 and belt 406 could be made as disposable items.

In another embodiment, instead of an RF current, the skin can be heated using optical energy. The optical energy can be produced by a laser, an incandescent lamp, a flash lamp, or a LED. The belt or roller may be made of transparent material, for example, glass, Polycarbonate, or Perspex™ enabling heating with light energy simultaneous with puncturing. Alternatively, light sources may be mounted to illuminate/irradiate from both sides of roller 208.

The present apparatus and method enable collagen remodeling due to fragmental stimulation of collagen growth in the skin using an electrical electrode and invasive pins.

While the method and apparatus have been described with respect to a limited number of embodiments, it will be appreciated that many variations, modifications and other applications of the method and apparatus may be made.

The invention claimed is:

1. A system for skin treatment, comprising:
   (a) an applicator for skin treatment, comprising:
      i) one or more RadioFrequency (RF) electrodes configured to be applied to skin surface; and
      ii) an article located between the electrodes, said article containing one or more protruding pins comprising one or more isolating or dielectric materials having a resistance greater than the skin resistance and electrically isolated from the RF electrodes, and operative to puncture and penetrate the skin; and
   (b) a control unit.

2. The system according to claim 1, wherein the article is made of electrically isolating material.

3. The system according to claim 1, wherein the protruding pins of the article are made from at least one member selected from the group consisting of metal, plastic, and a composite material.

4. The system according to claim 1, wherein the length of the pins is in a range of from 0.1 mm to 3 mm and the diameter of the pins is less than 0.5 mm.

5. The system according to claim 1, wherein the pins are designated to penetrate the skin.

6. The system according to claim 1, wherein the applicator further comprises a light source.

7. The system according to claim 6, wherein the light source is at least one member selected from the group consisting of an incandescent lamp, a flash lamp, a LED, and a laser.

8. The system according to claim 6, wherein the light source is arranged to illuminate the skin between the electrodes.

9. The system according to claim 1, wherein the RF electrodes communicate with a source of cooling fluid.

10. The system according to claim 1, wherein the control unit further comprises:
   (a) a source of RF energy;
   (b) a light emitting unit power supply; and
   (c) a source of cooling fluid.

11. The system according to claim 10, wherein the source of RF energy and the source of cooling fluid communicate with the one or more RF electrodes.

12. The system according to claim 10, wherein the light emitting unit power supply communicates with a light source.

* * * * *